United States Patent
Ergun

(10) Patent No.: US 10,182,925 B2
(45) Date of Patent: Jan. 22, 2019

(54) CARTILAGE SLICING APPARATUS

(71) Applicant: Onur Ergun, Ankara (TR)

(72) Inventor: Onur Ergun, Ankara (TR)

( * ) Notice: Subject to any disclaimer, the term of this patent is extended or adjusted under 35 U.S.C. 154(b) by 0 days.

(21) Appl. No.: 15/574,574

(22) PCT Filed: May 27, 2016

(86) PCT No.: PCT/TR2016/000074
§ 371 (c)(1),
(2) Date: Nov. 16, 2017

(87) PCT Pub. No.: WO2016/195610
PCT Pub. Date: Dec. 8, 2016

(65) Prior Publication Data
US 2018/0147072 A1 May 31, 2018

(30) Foreign Application Priority Data
May 29, 2015 (TR) .............................. a 2015 06542

(51) Int. Cl.
*B23P 19/04* (2006.01)
*A61F 2/46* (2006.01)
*A61B 17/16* (2006.01)
*A61F 2/30* (2006.01)
*A61B 17/00* (2006.01)

(52) U.S. Cl.
CPC ........ *A61F 2/4644* (2013.01); *A61B 17/1635* (2013.01); *A61B 2017/00969* (2013.01); *A61F 2/30756* (2013.01); *A61F 2002/3096* (2013.01)

(58) Field of Classification Search
CPC ... B23Q 1/00; B23Q 1/03; B23Q 1/25; B23Q 1/28; B23Q 1/66
See application file for complete search history.

(56) References Cited

U.S. PATENT DOCUMENTS

| | | | | |
|---|---|---|---|---|
| 4,735,245 A * | 4/1988 | Cox | ..................... | B23D 47/025 144/251.1 |
| 4,910,859 A * | 3/1990 | Holcomb | .............. | B23P 19/006 140/147 |
| 6,058,990 A * | 5/2000 | Kent | ........................ | B25H 1/10 144/1.1 |
| 8,276,895 B2 * | 10/2012 | Brown | ............... | B23K 37/0435 269/210 |
| 8,517,366 B2 * | 8/2013 | Seber | ........................ | B25B 1/24 269/172 |
| 2008/0255562 A1 | 10/2008 | Gil et al. | | |
| 2012/0191093 A1 | 7/2012 | Wong et al. | | |
| 2014/0364854 A1 | 12/2014 | Steinhardt et al. | | |
| 2018/0147072 A1* | 5/2018 | Ergun | ................... | A61F 2/4644 |

FOREIGN PATENT DOCUMENTS

EP 1 360 948 A1 11/2003
WO 2013/177389 A1 11/2013

OTHER PUBLICATIONS

EP 1360948_English_Abstract.

* cited by examiner

*Primary Examiner* — Lee D Wilson
(74) *Attorney, Agent, or Firm* — Ladas & Parry LLP

(57) ABSTRACT

The present invention relates to a cartilage slicing apparatus which enables cartilage pieces to be sliced with a form and thickness so as to be used in surgery.

7 Claims, 6 Drawing Sheets

CARTILAGE SLICING APPARATUS

RELATED APPLICATION

This application is a national phase entry under 35 USC 371 of International Patent Application No.: PCT/TR2016/000074 filed on 27 May 2016, which claims priority from Turkish Patent Application No. 2015/06542 filed on 29 May 2015, the disclosures of which are incorporated herein by reference in their entirety.

TECHNICAL FIELD

The present invention relates to a cartilage slicing apparatus which enables cartilage pieces to be sliced with a form and thickness so as to be used in surgery.

BACKGROUND OF THE INVENTION

Cartilage is used as graft material in myringoplasty, tympanoplasty and many other ear surgeries. In these operations, a cartilage obtained from one's own is usually preferred and the cartilage obtained is required to be formed suitably. During this forming operation, it is also tried to utilize a limited amount of cartilage graft with as little loss as possible while it is tried to give a desired form to the cartilage precisely. Although the result desired to be reached may vary in accordance with the specific requirements of different surgeries, thin and smooth-surface layers are usually preferred. The desired thickness mostly requires to slice the cartilage in 0.2-0.4 mm thickness. Despite the fact that this is the desired result, it is very difficult to obtain cartilage slices with desired thickness and uniformity via a manual cartilage slicing method.

There are some cartilage slicing devices developed in the state of the art in order to solve this problem. Although cartilage slices with desired thickness can be obtained by these devices, the said designs have some limitations. In the most frequently encountered design of cartilage slicing device, the device has fixed plates like clamp which compresses the cartilage from two sides. After the cartilage is fixed in a desired position by washers with predetermined thicknesses—which are used for controlling thickness of the slice and placed next to it the cartilage is sliced by passing a blade suitable for the device through the cartilage.

Some of the problems confronted by this design are as follows: only one slice can be received from the cartilage at a time; it is required to open and re-prepare the device afterwards; it can only be used with a special blade having its own consumable material; it necessitates a large number of positioning washers which are prone to loss or bending and have different thicknesses; and most importantly, it is crushed due to the wall thickness of the blade passing through the cartilage which is fixed among the clamping plates, to a certain extent.

A cartilage piece desired to be sliced is mostly thinner than 1 millimeter. Whereas surgical blades usually have approximately 0.4 mm thickness. This indicates that the cartilage will be substantially crushed while a blade is passing through thereof in the event that it is fixed from its both sides. And crushed cartilages lose their structural strength. With the purpose of being a solution for the problem of crushing while cutting cartilage, positioning washers are made as perforated in some designs wherein fixed clamping washers are used. The cartilage, which is compressed while the blade is cutting the cartilage, is forced to replace inwards these perforations instead of being entirely crushed. In conclusion, a slice which is a less crushed but has a wavy surface is obtained.

The United States patent document no. US2014/0364854, an application in the state of the art, discloses a disposable cartilage cutter. The medical cutting device disclosed in the said patent document enables to produce cartilages thinner than big cartilages and it is preferably made of a sterilizable material such as sterilizable plastic. The cutting devices comprise device body and cover. The device body comprises a first holding device with a first working section having a first recess disposed on a thereof. The said first recess is entirely enclosed by a first delimiting ridge or it is partially enclosed by a plurality of ridges.

The United States patent document no. US2012/0191093, an application in the state of the art, discloses an apparatus and method for cutting costal cartilage. The invention disclosed in the said patent document enables to reduce the skill and the time required, while it increases the uniformity of the cut slices for obtaining cartilage slices. In addition, slices are obtained precisely from the central core of the rib via an adjustable guide. The present device comprises three main components: a cutting jig, a slide member and a base. When the slide member and base are coupled together, a specimen assembly is formed. The cutting jig comprises two substantially U-shaped halves, namely a top half and a bottom half. The bottom half of the cutting jig comprises a substantially T-shaped jig key on its outer edge. It helps the key cutting jig to be guided along through the specimen assembly. There is a pair of parallel blades separated from each other by a pair of aluminium spacers between the bottom half and the top half. The bottom and top halves have the blades and the spacers there between and they enable to define an aperture in the center of the cutting jig due to their U-shape. The spacers enable the blades to be in a fixed distance apart and ensure that an aperture or cutting segment which is used to cut a cartilage specimen is defined. The cutting jig and the blades are held in a locked position with the aid of a pair of bolts inserted through both the top and the bottom halves.

SUMMARY OF THE INVENTION

An objective of the present invention is to realize a cartilage slicing apparatus which enables cartilage pieces used in surgical operations to be sliced with a desired thickness, smooth surface and in an uncrushed way.

DETAILED DESCRIPTION OF THE INVENTION

"A Cartilage Slicing Apparatus" realized to fulfil the objectives of the present invention is shown in the figures attached, in which.

Figure 1:
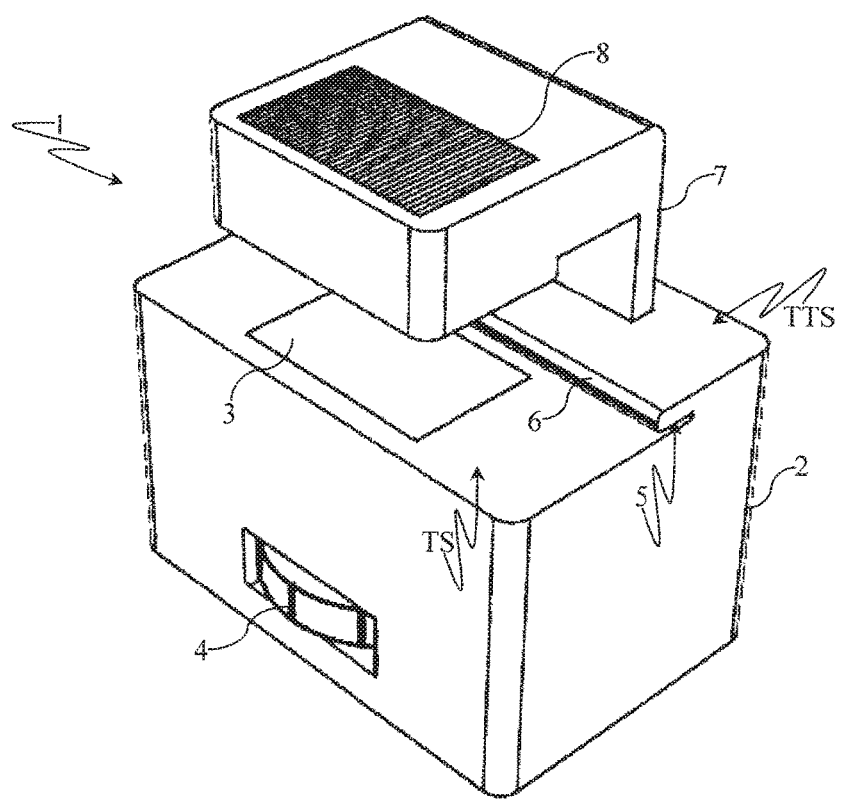
FIG. 1 is a perspective view of the cartilage slicing apparatus in accordance with the present invention when the top cover is in upper position.

The components illustrated in the figures are individually numbered, where the numbers refer to the following:
1. Cartilage slicing apparatus
2. Body
3. Table
4. Positioning member
5. Channel
6. Tab
7. Top cover
8. Movable fixing member TS: Top surface of the body
TTS: Top surface of the tab
K: Cutting member The cartilage slicing apparatus (1) in accordance with the present invention comprises:
- at least one body (2);
- at least one table (3) which is located on the top surface (TS) the body (2) and whereon the cartilage desired to be sliced is placed;
- at least one positioning member (4) which is located on the body (2), connected to the table (3) by means of suitable connection members and enables to move the table (3) in a vertical plane;
- at least one tab (6) which is integrated to the body (2), extends parallel to the body (2) such that there will be a gap to form a channel (5) between the top surface (TS) of the body (2) and itself on the top surface (TS) of the body (2);
- at least one housing (not shown in the figures) which is located on the top surface (TTS) of the tab (6);
- at least one top cover (7) which is inserted into the housing such that it will be able to move in a vertical plane and enables to fix the cartilage—that is placed onto the table (3)—during the slicing operation;
- a plurality of movable fixing members (8) which are located on the top cover (7), move in a vertical plane depending on the thickness of the cartilage on the table (3) and prevent, the cartilage from being crushed during the cutting operation.

In the inventive cartilage slicing apparatus (1) the body (2) includes at least one table (3) which can move in a vertical plane throughout the body (2) on its top surface (TS). The cartilage piece desired to be cut is placed onto the said table (3). Thickness of the cartilage, which is placed onto the table (3), desired to be cut is provided by moving the table (3) in a vertical plane according to the body (2). The positioning member (4) is placed on the body (2) and connected to the table (3) by means of suitable connection members which will enable to move the table (3) in a vertical plane. In a preferred embodiment of the invention, the positioning member (4) is a member with a wheel form. The tab (6) is integrated to the body (2) and it extends parallel to the top surface (TS) of the body (2) such that there will be a gap between the top surface (TS) of the body (2) and itself so that the channel (5) that will enable to guide a cutting member (K) like blade for cutting the cartilage is formed. There is at least one housing on the top surface (TTS) of the tab (6). At least one top cover (7) which enables to keep the cartilage—desired to be cut—fixed during cutting without being crushed and can move in a vertical plane is inserted into the said housing. On the top cover (7), there are a plurality of movable fixing members (8) which come upon the cartilage placed on the table (3) and enable to keep the cartilage fixed without being crushed during the cutting operation by moving in a vertical plane depending on the thickness of the said cartilage.

Figure 2:
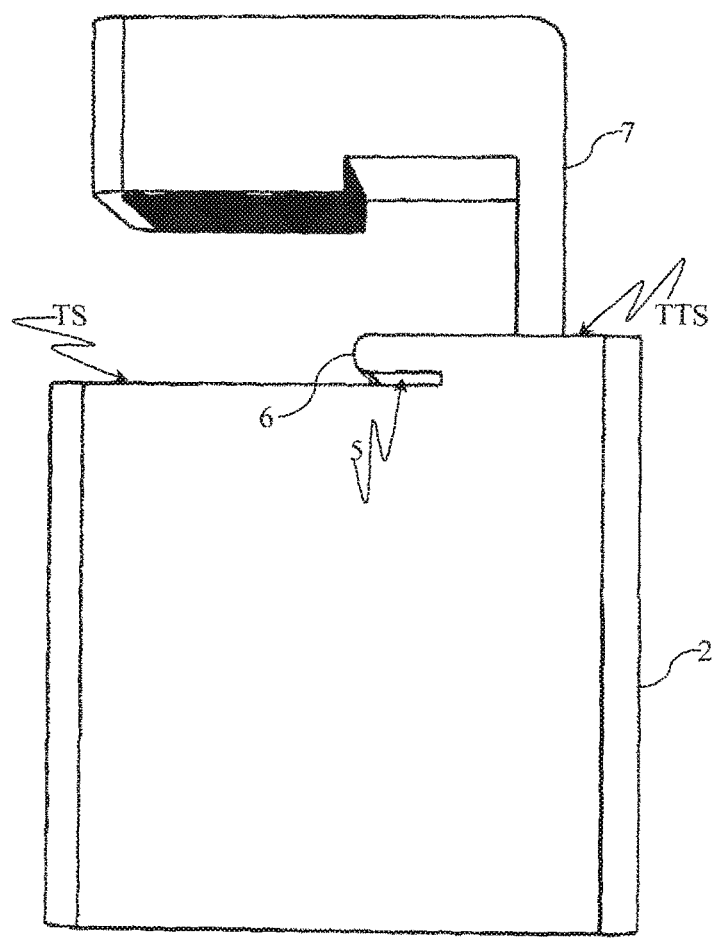
FIG. 2 is a side view of the cartilage slicing apparatus in accordance with the present invention when the top cover is in upper position.
Figure 3:
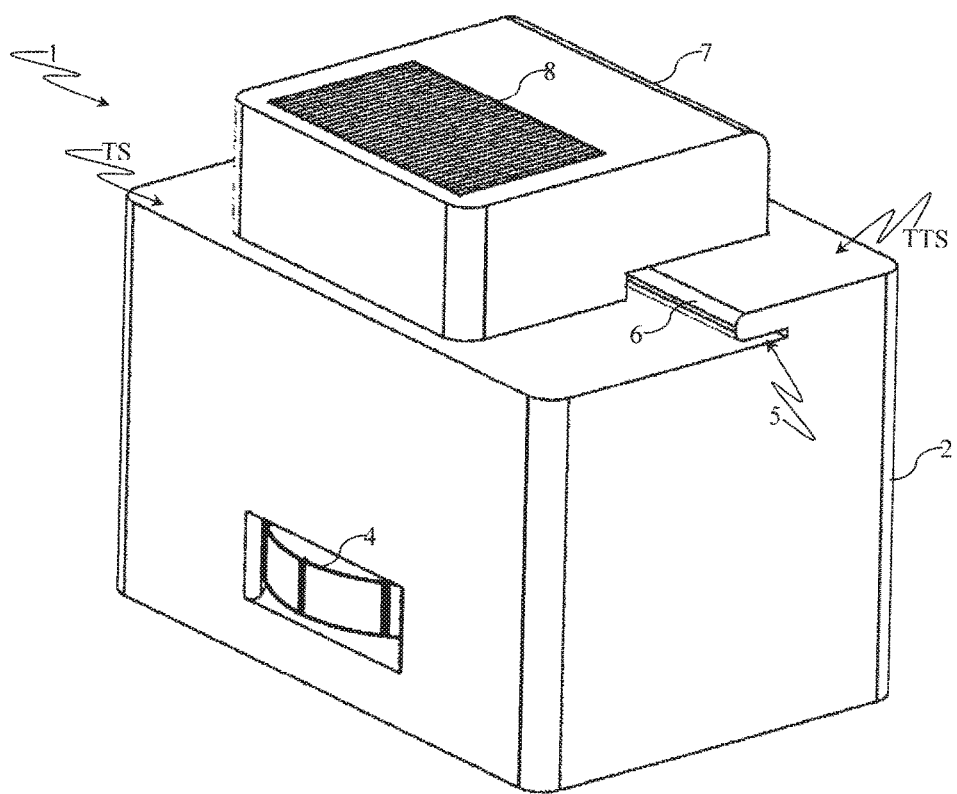
FIG. 3 is a perspective view of the cartilage slicing apparatus in accordance with the present invention when the top cover is in lower position.
Figure 4:
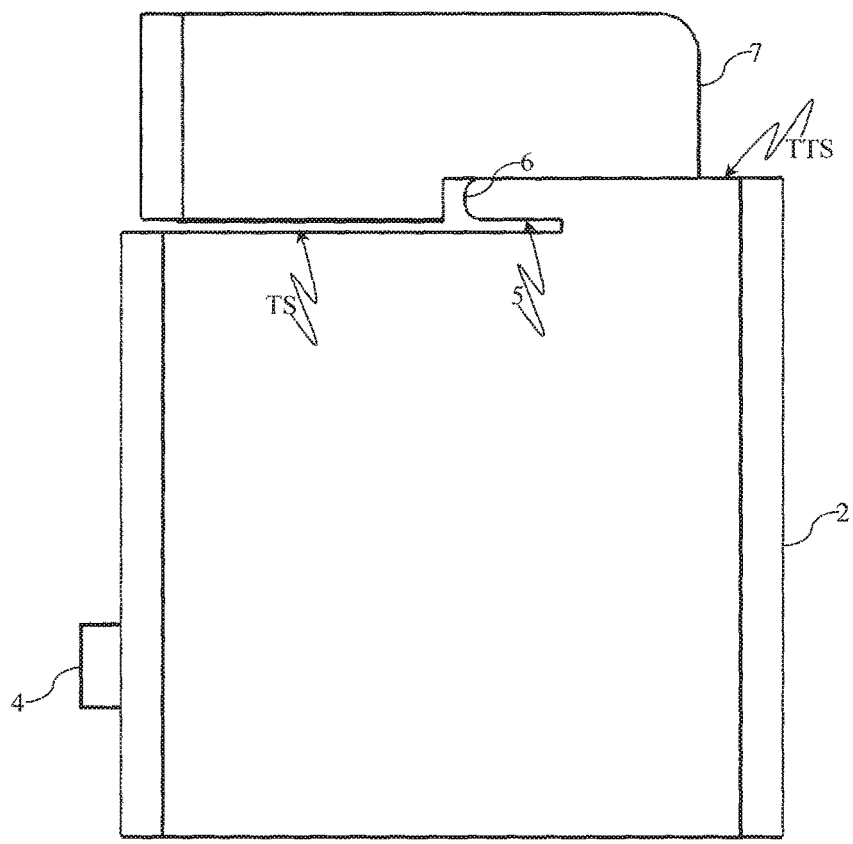
FIG. 4 is a side view of the cartilage slicing apparatus in accordance with present invention when the top cover is in lower position.
Figure 5:
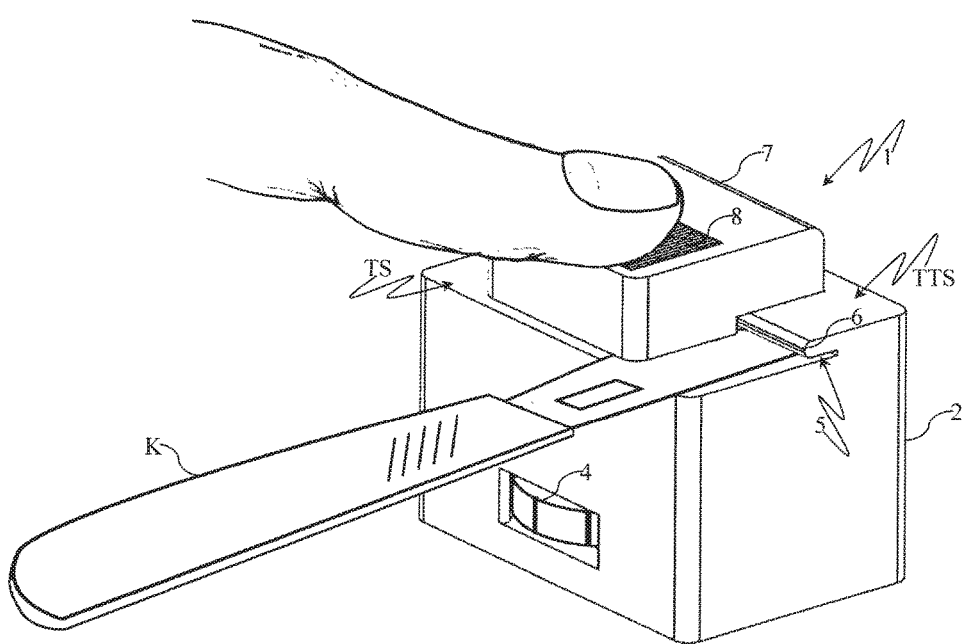
FIG. 5 is a perspective view of the cartilage slicing apparatus in accordance with the present invention during the cartilage cutting process.

When a cartilage cutting is to be performed by using the cartilage slicing apparatus (1), the top cover (7) which can move in a vertical plane is lifted upwards and the cartilage piece desired to be cut is placed onto the table (3) (FIG. 1 and FIG. 2). The table (3) is then moved in a vertical plane by means of the positioning member (4) and it is taken into the same height, i.e. zero position, with the top surface (TS) of the body (2). Thereupon, the top cover (7) is lowered down, i.e. towards the body (2), by being moved in a vertical plane inside the housing (FIG. 3 and FIG. 4). Afterwards, the table (3) is lowered down in a vertical plane throughout the body (2) by means of the positioning member (4) in order to determine the thickness whereby it is desired to cut the cartilage and to adjust this thickness. Due to the fact that the table (3) can move in a vertical plane, it is ensured that the cartilage can be taken into a suitable position so as to be cut at a desired thickness without needing any positioning washer and the necessity that the cartilage to be obtained has to depend on intermediate values is eliminated. The top cover (7) becomes in the same level with the tab (6) while its lower surface is in a lowered position and a gap inside which a cutting member (K) such as blade can move is formed between the top surface (TS) of the body (2) and itself. A cutting member (K) such as blade is inserted into the channel (5) formed between the tab (6) and the top surface (TS) of the body (2) while the cartilage is being hold in a fixed way by slightly pressing onto the movable fixing members (8) and the cartilage is cut in a desired thickness by proceeding it on the top surface (TS) of the body (2) in a horizontal plane throughout the channel (5) (FIG. 5). The movable fixing members (8) which can move in the vertical plane corresponding onto the cutting member (K) rise and enable the cartilage not to be crushed as the cutting member (K) proceeds while the cartilage is being cut and they also ensure that pressure necessary for keeping the cartilage fixed is applied at the same time. If it is desired to cut one more slice after the cutting operation is ended, the table (3) is lowered down up to the desired slice thickness by means of the positioning member (4) and one more slice is cut as described above without needing to open the top cover (7) and to remove the cut slice. After a desired number of slice is prepared, the top cover (7) is lifted upwards and the cartilage slice/s located on the table (3) are removed.

Due to the fact that the table (3) included in the inventive cartilage slicing apparatus (1) and whereon the cartilage is placed is movable in a vertical plane, the table (3) can be taken into a position suitable for cutting a cartilage with desired thickness without needing and positioning washer. A positioning member (4) such as wheel, which controls the movement of the table (3), enables to control the position of the table (3) precisely. In addition, contrary to designs which use positioning washers included in the state of the art, thickness of the cut cartilage does not have to depend on some intermediate values by means of the movable table (3) in the inventive apparatus (1).

Figure 6:
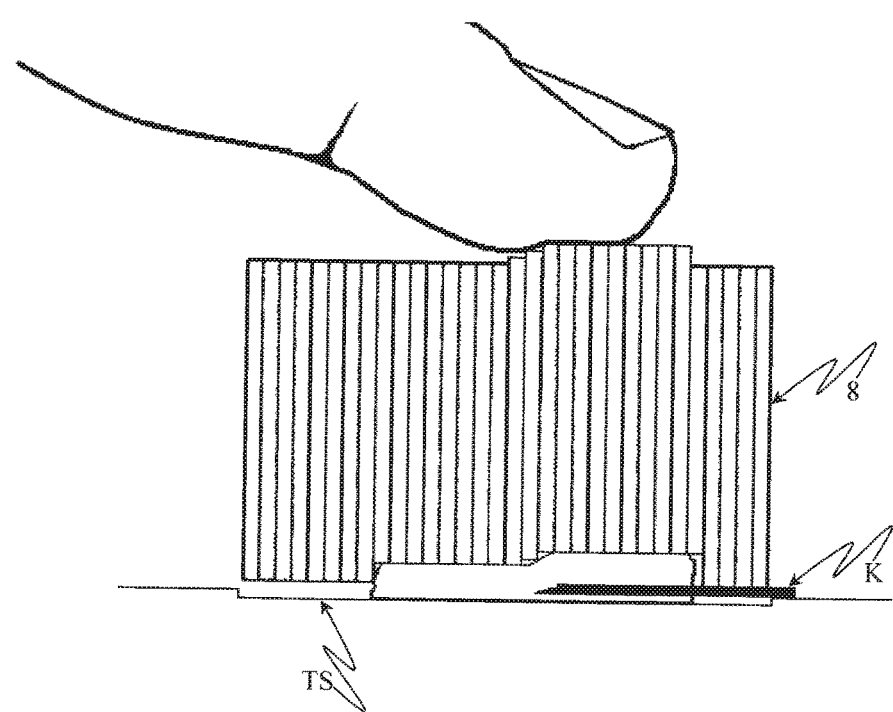
FIG. 6 is a detailed view of the movable fixing member included in the cartilage slicing apparatus in accordance with the present invention.

While the cartilage is being fixed by the table from the lower part, it is also enabled to fix the top surfaces by the user by pressing over the top surfaces by finger via the movable fixing members (8) which are arranged side by side and in a vertical axis. The said movable fixing members (8) enable the user to feel the cartilage and the cutting member (K) passing through thereof during the cutting process and follow it. At the same time, the cartilage is prevented from being crushed upon the movable fixing members (8) in the line where the cutting member (K) is located rise as the cutting member (K) proceeds and continue create a certain pressure for the cartilage at that point (FIG. 6).

The top cover (7) holding together the movable fixing members (8) can move in a vertical plane. Thus, an opportunity for accessing the table (3) is provided in order to place the cartilage to be cut into the table (3) and to remove the cartilage slices cut while the top cover (7) is in risen position. While the top cover (7) is in lowered position, a gap remains between the top surface (IS) of the body (2) and itself such that only the cutting member (K) can pass through and thus the plane where the cutting member (K) can move is determined.

Within these basic concepts, it is possible to develop a great variety of embodiments of the inventive "Cartilage Slicing Apparatus (1)"; it cannot be limited to the examples disclosed herein and it is essentially according to the claims.

The invention claimed is:

1. A cartilage slicing apparatus (1) enabling cartilage pieces to be sliced with a form and thickness in accordance with surgical use of the cartilage pieces; comprising
    at least one body (2);
    at least one table (3) which is located on a top surface (TS) of the body (2) and on which cartilage desired to be sliced can be placed;
    at least one positioning member (4) which is located on the body (2) and connected to the table (3) such that adjustment of the positioning member moves the table (3) in a vertical plane;
    at least one tab (6) which is integrated to the body (2) and extends parallel to the top surface of the body (2) to form a channel (5) between the at least one tab (6) and the top surface (TS) of the body (2);
    at least one top cover (7) disposed atop a top surface (TTS) of the tab (6) and movable in a vertical plane to fix the cartilage that is placed onto the table (3) during a slicing operation;
    a plurality of fixing members (8) which are located on the top cover (7), and which are movable in a vertical plane such that, with the top cover fixing the cartilage upon the table, the fixing members can adjust to a thickness of the cartilage on the table (3) and prevent the cartilage from being crushed during the slicing operation.

2. A cartilage slicing apparatus (1) according to claim 1, characterized by at least one table (3) which is located on the top surface (TS) of the body (2), can move in a vertical plane throughout the body (2) and whereon the cartilage desired to be sliced is placed.

3. A cartilage slicing apparatus (1) according to claim 1, characterized by the positioning member (4) which is located on the body (2) and connected to the table (3) by means of suitable connection members to move the table (3) in a vertical plane.

4. A cartilage slicing apparatus (1) according to claim 3, characterized by the positioning member (4) which has a wheel form.

5. A cartilage slicing apparatus (1) according to claim 1, characterized by a tab (6) which is integrated to the body (2) and extends parallel to the top surface (TS) of the body (2) such that there will be a gap between the top surface (TS) of the body (2) and itself so that the channel (5) that will enable to guide a cutting member (K) like blade for cutting the cartilage is formed.

6. A cartilage slicing apparatus (1) according to claim 1, characterized by at least one top cover (7) which is inserted into the housing located on the top surface (TTS) of the tab (6), enables to keep the cartilage—desired to be cut—fixed during cutting without being crushed and can move in a vertical plane.

7. A cartilage slicing apparatus (1) according to claim 1, characterized by a plurality of movable fixing members (8) which are located on top cover (7), move in a vertical plane depending on the thickness of the said cartilage by coming upon the cartilage located on the table (3) and thus enable to keep the cartilage fixed without being crushed during the cutting operation.

* * * * *